United States Patent [19]
Allais et al.

[11] 3,979,515
[45] Sept. 7, 1976

[54] NOVEL DIBENZO(B,F)AZEPINES AS THYMOANALEPTICS

[75] Inventors: Andre Allais, Les Lilas; André Poittevin, Vaires sur Marne, both of France

[73] Assignee: Roussel-UCLAF, Paris, France

[22] Filed: Dec. 18, 1974

[21] Appl. No.: 533,846

Related U.S. Application Data

[62] Division of Ser. No. 40,410, May 25, 1970, abandoned.

[30] Foreign Application Priority Data

May 28, 1969 France.................... 69.17373

[52] U.S. Cl............................. 424/244; 260/239 D
[51] Int. Cl.²................... A61K 31/33; C07D 9/00; C07F 9/00
[58] Field of Search.............. 424/244; 260/239 D

[56] References Cited
UNITED STATES PATENTS 3,501,459  3/1970  Sheidler et al................ 260/239 D

*Primary Examiner*—Stanley J. Friedman
*Attorney, Agent, or Firm*—Hammond & Littell

[57] ABSTRACT

Novel 5-methyl-10-(β-alkylaminoethyl)dibenzo(b,f) azepines of the formula

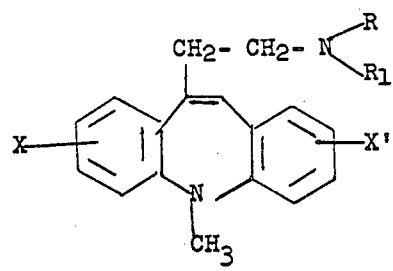

wherein R is lower alkyl, $R_1$ is selected from the group consisting of hydrogen and lower alkyl and X and X' are selected from the group consisting of hydrogen and halogen and their non-toxic, pharmaceutically acceptable acid addition salts having a superior thymoanaleptic activity and their preparation and use.

10 Claims, No Drawings

NOVEL DIBENZO(B,F)AZEPINES AS THYMOANALEPTICS

PRIOR APPLICATION

This application is a division of copending U.S. Pat. application Ser. No. 40,410 filed May 25, 1970, now abandoned in favor of continuation application Ser. No. 523,978, filed Nov. 15, 1974.

STATE OF THE ART

Dibenzoazepines, as a class, have been known for their anti-depressive properties and the best known are imipramine, desipramine and dibenzepine. This type of product is characterized by its thymoanaleptic action such as the possibility of reversing the moods observed in melancholy, anxious or neurasthenic patients. Dibenzoazepines generally have a certain advantage over monoamainooxydasis inhibitors whose effects are less constant and which are frequently accompanied by dangerous side effects. The known dibenzoazepines, however, have the disadvantage of also varying degrees of sedative psycholeptic activity or anticholinergic action depending upon the molecule.

OBJECTS OF THE INVENTION

It is an object of the invention to provide novel dibenzoazepines of formula I having a superior thymoanaleptic activity.

It is another object of the invention to provide a novel process for the preparation of diazoazepines of formula I and novel intermediates produced therein.

It is a further object of the invention to provide novel thymoanaleptic compositions and to a novel method of inducing a thymoanaleptic activity in warm-blooded animals.

These and other objects and advantages of the invention will become obvious from the following detailed description.

THE INVENTION

The novel compounds of the invention are 5-methyl-10-($\beta$-alkylaminoethyl)dibenzo($b,f$) azepines of the formula

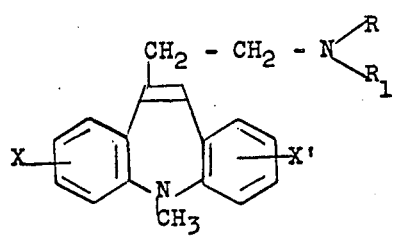

wherein R is lower alkyl, $R_1$ is selected from the group consisting of hydrogen and lower alkyl and X and X' are selected from the group consisting of hydrogen and halogen and their non-toxic, pharmaceutically acceptable acid addition salts. Particularly preferred are the compounds wherein R is alkyl of 1 to 4 carbon atoms, $R_1$ is hydrogen or alkyl of 1 to 4 carbon atoms and X and X' are hydrogen, chlorine, bromine and iodine.

Examples of suitable acids for the non-toxic, pharmaceutically acceptable acid addition salts are organic acids such as citric acid, malic acid, benzoic acid, fumaric acid, acetic acid and inorganic acids such as hydrochloric acid, hydrobromic acid, phosphoric acid, etc.

Preferred dibenzoazepines of formula I are 5-methyl-10-($\beta$-dimethylaminoethyl)-dibenzo ($b,f$) azepine and its hydrochloride; 5-methyl-10-($\beta$-monomethylaminoethyl)-dibenzo ($b,f$) azepine and its hydrochloride; 2-chloro-5-methyl-10-($\beta$-dimethylaminoethyl)-dibenzo($b,f$)azepine and its fumarate; 7-chloro-5-methyl-10-($\beta$-dimethylaminoethyl)-dibenzo ($b,f$) azepine and its fumarate; 7-chloro-5-methyl-10-($\beta$-monomethylaminoethyl)-dibenzo ($b,f$) azepine and its fumarate; and 8-chloro-5-methyl-10-($\beta$-dimethylaminoethyl)-dibenzo ($b,f$) azepine and its fumarate.

The novel process of the invention for the preparation of the dibenzo ($b,f$) azepines of formula I comprises reducing a salt of 9-alkoxycarbonyl-10-methyl acridinium of the formula

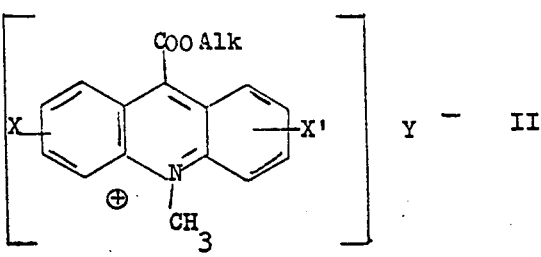

wherein X and X' have the above definition and Alk is alkyl of 1 to 4 carbon atoms and Y is an anion with a reducing agent selected from the group consisting of alkali metal borohydride and hydrogen in the presence of a catalyst to form the corresponding 9-alkoxycarbonyl-10-methyl-acridane of the formula

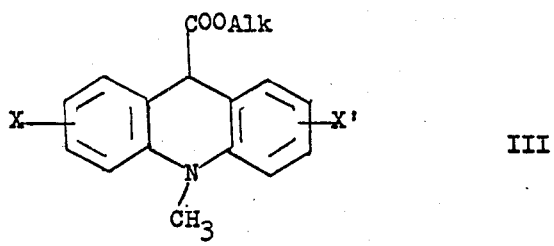

reacting the latter with a 2-halo-1-(dialkylamino)ethane wherein the halogen is selected from the group consisting of bromine, chlorine and iodine in the presence of an alkaline agent selected from the group consisting of alkali metals and alkali metal alcoholates to form a compound of the formula

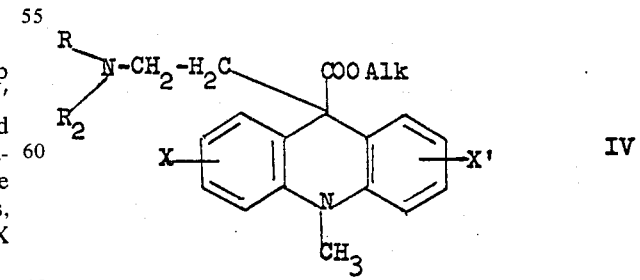

wherein X, X' and R have the above definitions and $R_2$ is lower alkyl, reducing the latter with a compound selected from the group consisting of lithium aluminum hydride, aluminum hydride, diborane and an organo aluminum hydride to obtain a 9-hydroxymethyl-9-(β-dialkylaminoethyl)-10-methyl-acridane of the formula

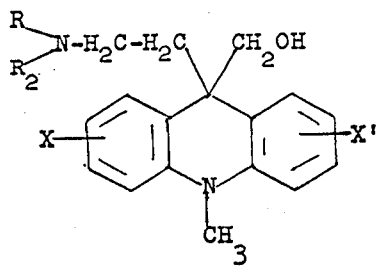

V wherein X, X' R and $R_2$ have the above definitions and treating the latter with a dehydrating agent to obtain the corresponding 5-methyl-10(β-dialkylaminoethyl)-dibenzo (b,f) azepine of the formula

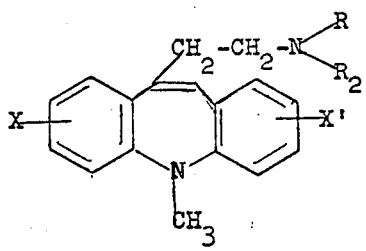

VI wherein X, X', R and $R_2$ have the above definitions. The said product can be reacted with an acid to form the corresponding acid addition salt or treated with a dealkylating agent selected from the group consisting of a lower alkyl chloroformate and a cyanogenhalide followed by alkaline treatment to obtain the corresponding dibenzoazepine of the formula

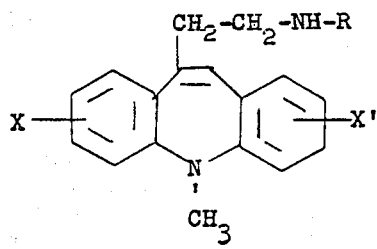

VII wherein X, X' and R have the above definitions which can be reacted with an acid to form the corresponding acid addition salt.

In preferred modes of the process, the reducing agent is an alkali metal borohydride such as potassium borohydride or sodium borohydride, the hydrogenation catalyst may be a platinum or palladium catalyst; the alkaline agent may be an alkali metal such as potassium or sodium or an alkali metal alcoholate such as potassium tert.-butylate; the organo aluminum hydride may be diisobutyl aluminum hydride or triisobutylaluminum hydride; the dehydration agent may be a Lewis acid, sulfuric acid, phosphoric acid or its anhydride or p-toluene sulfonic acid; the lower alkyl chloroformate may have an alkyl of 1 to 4 carbon atoms; the cyanogenhalide may be cyanogenchloride or cyanogenbromide and the alkaline treatment may be effected with sodium hydroxide or potassium hydroxide. The 9-alkoxycarbonyl 9-(β-dialkylaminoethyl)-10-methyl-acridane of formula IV may be purified by forming a salt of the said compound, their freeing the base with a basic agent such as sodium hydroxyde, preferably the said salt is derived from an organic dicarboxylic acid such as fumaric acid.

The starting materials for the process of the invention, salts of 9-alkoxycarbonyl-10-methyl acridinium, can be prepared by a process analogous to that of Rauhut et al (J. Org. Chem., Vol. 30, 1965, p. 3587) and the preferred salts are the chlorides, sulfates and methosulfates.

The novel thymoanaleptic compositions having little side effects are comprised of at least one 5-methyl-10-(β-alkylaminoethyl)-dibenzo (b,f) azepine of formula I and a pharmaceutical carrier. The compositions may be in the form of injectable solutions or suspensions, suppositories, compressed tablets or coated tablets formed in the usual manner. The usual daily dose for the adult is 25 to 500 mg depending upon the specific compound and the method of administration. The compressed tablets generally contain about 25 mg of the active compound.

The compositions have a perceptibly superior thymoanaleptic activity compared to benzepine. This has been shown in animals by the antagonistic effect against neuroleptics such as reserpine and tetrabenazine and a potentialization effect against amphetamine and dihydroxyphenylalanine (DOPA) in animals first sensitized by a monoaminooxydasis inhibitor. The compositions may be administered without fear of observing in patients the drowsiness due to sedative effects or vision disturbances of the atropine type.

The novel method of the invention for inducing thymoanaleptic activity in warm-blooded animals comprises administering to warm-blooded animals an effective amount of at least one compound of formula I. They may be administered orally, transcutaneously or rectally. The usual dosage is 0,4 to 1,6 mg/kg.

In the following examples there are described several preferred embodiments to illustrate the invention. However, it should be understood that the invention is not intended to be limited to the specific embodiments.

EXAMPLE I

PREPARATION OF
5-methyl-10-(β-dimethylaminoethyl)-Dibenzo (b,f) azepine

STEP A: 9-methoxycarbonyl-10-methyl-acridane 80 gm of potassium borohydride were added over 45 minutes at room temperature to a mixture of 800 cc of ethanol, 40 cc of distilled water and 78 gm of the methosulfate of 9-methoxycarbonyl-10-methyl-acridinium [made by process of Rauhut et al, J. Org. Chem., Vol. 30 (1965), p. 3587] and after stirring for 30 minutes, the mixture was poured into ice-water mixture and stirred for 2 hours. The reaction mixture was extracted with ether and the ether extracts were distilled to dryness in vacuo to obtain 51 gm of 9-methoxycarbonyl-10-methyl-acidane melting at 106°C.

The product occurred in the form of a pale yellow solid soluble in methylene chloride, ether and ethyl acetate and insoluble in water. For analysis, the product was recrystallized from hot and cold isopropyl ether after which the melting point was unchanged.

Analysis: $C_{16}H_{15}O_2N$; molecular weight = 253.31
Calculated: %C 75.87 %H 5.87 %N 5.63
Found: 75.9 5.9 5.7

I.R. SPECTRUM (Chloroform):
Presence of C=O at 1728 cm$^{-1}$
Presence of aromatic at 1595 and 1475 cm$^{-1}$
As far as is known, this product is not described in the literature.

STEP B: Fumarate of 9-methoxycarbonyl-9-($\beta$-dimethylaminoethyl)-10-methyl-acridane 250 cc of sodium hydroxide was added to a cold mixture of 250 cc of water and 250 gm of 2-chloro-1-dimethylaminoethane hydrochloride while keeping the temperature below +10°C. After stirring for 30 minutes at 5°C, the reaction mixture was extracted with ether and the ether extract was washed with water, dried over magnesium sulfate and the ether was distilled off. The residue was rectified to obtain 130 gm of 2-chloro-1-dimethylaminoethane having a boiling point of 106°–108°C.

50 cc of toluene were distilled off a mixture of 36.5 gm of 9-methoxycarbonyl-10-methyl-acridane and 1000 cc of toluene and the mixture was then cooled and 5.65 gm of potassium were added thereto at a temperature below +10°C. After stirring for 2 hours at room temperature, the reaction mixture was refluxed for 30 minutes and then was cooled. At a temperature below 20°C, a solution of 52.5 cc of 2-chloro-1-dimethylaminoethane in 200 cc of toluene was added to the reaction mixture which was heated at reflux for 20 hours and then cooled. 100 cc of tert.-butanol were added thereto and after stirring for one hour at room temperature, 35 cc of ethanol were added thereto and stirring was continued for 30 minutes at room temperature. The reaction mixture was extracted with 2N hydrochloric acid and the acid extract was washed with ether and made alkaline by the addition of sodium hydroxide. The mixture was extracted with ether and the ether extract was washed with water, dried over magnesium sulfate and was distilled to dryness under vacuo. The residue was dissolved in 100 cc of methanol and 300 cc of a saturated solution of fumaric acid in methanol were added thereto. The reaction mixture was then distilled and the methanol coming off was replaced with ethyl acetate. When crystallization started, the mixture was iced for 30 minutes and then was filtered. The precipitate was washed with water and dried to obtain 37 gm of the fumarate of 9-methoxycarbonyl-9-($\beta$-dimethylaminoethyl)-10-methyl-acridane melting at 176°C.

The product occurred in the form of a solid product soluble in methanol, slightly soluble in ethyl acetate and insoluble in water. For analysis, the product was recrystallized by dissolution in methanol, addition of ethyl acetate and concentration. The melting point did not change.

Analysis: $C_{24}H_{28}O_6N_2$; molecular weight = 440.48
Calculated: %C 65.44 %H 6.41 %N 6.36
Found: 65.5 6.4–6.3 6.3–64

I.R. SPECTRUM (Nujol)
Presence of C=O bands at 1728 cm$^{-1}$ (ester) and at 1700 cm$^{-1}$ (acid)
As far as is known, this compound is not described in the literature.

STEP C: 9-hydroxymethyl-9-($\beta$-dimethylaminoethyl)-10-methyl-acridane 50 gm of the fumarate of 9-methoxycarbonyl-9-($\beta$-dimethylaminoethyl)-10-methyl-acridane were suspended in 500 cc of water and after cooling, 30 cc of sodium hydroxide were added thereto. The reaction mixture was extracted with methylene chloride and the organic phase was washed with water, dried over magnesium sulfate and was distilled to dryness in vacuo to obtain 36 gm of 9-methoxycarbonyl-9-($\beta$-dimethylaminoethyl)-10-methyl-acridane.

20 gm of lithium aluminum hydride were added over 15 minutes to iced 400 cc of tetrahydrofuran and then a solution of 36 gm of 9-methoxycarbonyl-9-($\beta$-dimethylaminoethyl)-10-methyl-acridan in 400 cc of tetrahydrofuran was added thereto over 30 minutes. The mixture was refluxed for 2 hours, then refrigerated and 200 cc of tetrahydrofuran containing 20% water were added thereto at a temperature below 0°C. The mixture was filtered and the filtrate was washed with methylene chloride and distilled to dryness in vacuo. The residue was dissolved in methylene chloride and the organic phase was washed with water, dried over magnesium sulfate and concentrated while adding ethyl acetate to replace the methylene chloride. Crystallization started and after icing for one hour the mixture was filtered. The precipitate was washed with water and was dried to obtain 24.5 gm of 9-hydroxymethyl-9-($\beta$-dimethylaminoethyl)-10-methyl-acridane melting at 150°C. Concentration of the mother liquor gave a second crop of 1.6 gm of the product for a total yield of 79%.

The product occurred in the form of a colorless solid soluble in methylene chloride, slightly soluble in ethyl acetate and insoluble in water. For analysis, the product was recrystallized by dissolution in methylene chloride and addition of ethyl acetate. The melting point remained unchanged.

Analysis: $C_{19}H_{24}ON_2$ — Molecular weight = 296.40
Calculated: %C 76.99 %H 8.16 %N 9.45
Calculated with 1/4 mole of ethyl acetate: 75.5 8.2 8.8
Found: 75.3–75.4 8.5–8.1 8.8–8.6

I.R. SPECTRUM: (chloroform)
Presence of -N< at 2780 cm$^{-1}$
Presence of -OH
As far as is known, this compound is not described in the literature.

STEP D: 5-methyl-10-($\beta$-dimethylaminoethyl)-dibenzo (b,f) azepine (b,f)

A mixture of 24.5 gm of 9-hydroxymethyl-9-($\beta$-dimethylaminoethyl)-10-methyl-acridane in a liter of m-xylene and 125 gm of phosphoric acid anhydride was heated at reflux for 3 hours and after cooling, the reaction mixture was poured over ice. The mixture was stirred for 15 minutes and was made alkaline by the addition of sodium hydroxide. The mixture was extracted with ethyl acetate and the ethyl acetate was washed with water, dried over magnesium sulfate and distilled to dryness in vacuo. The residue was dissolved in ether and the solution was filtered and concentrated to a small volume and pentane was added while distilling off the ether. After filtering, the filtrate was concentrated to about 100 cc and crystallization was started with icing for one hour. After filtering, the precipitate was washed with water and dried in vacuo to obtain 16 gm (70% yield) of 5-methyl-10-(β-dimethylaminoethyl)-dibenzo (b,f) azepine melting at 78°C.

The product occurred in the form of a yellow solid soluble in alcohols, ether, ethyl acetate and chlorinated solvents, slightly soluble in pentane and insoluble in water. For analysis, the product was subjected to chromatography on magnesium silicate and eluted with ether and was then recrystallized from hot and cold pentane. The melting point remained unchanged.

Analysis: $C_{19}H_{22}N_2$; molecular weight = 278.38
| | %C | %H | %N |
|---|---|---|---|
| Calculated: | 81.97 | 7.97 | 10.06 |
| Found: | 82.0 | 7.9 | 9.9 |

IR SPECTRUM: (chloroform)
Presence of C = C at 1634 cm$^{-1}$
Presence of - N<
U.V. SPECTRUM:

| Ethanol | |
|---|---|
| Max. at 215 mμ | $E_{1cm}^{1\%} = 932$ |
| Inflexion towards 281 mμ | $E_{1cm}^{1\%} = 156$ |
| Max. at 254–255 mμ | $E_{1cm}^{1\%} = 1122$ |
| Max. at 331 mμ | $E_{1cm}^{1\%} = 47$ |
| Ethanol — 0.1N HCl | |
| Max. at 214–215 mμ | $E_{1cm}^{1\%} = 929$ |
| Inflexion towards 280–281 mμ | $E_{1cm}^{1\%} = 167$ |
| Max. at 252–253 mμ | $E_{1cm}^{1\%} = 1074$ |
| Inflexion towards 326–327 mμ | $E_{1cm}^{1\%} = 46$ |
| Ethanol — 0.1N NaOH | |
| Max. at 254 mμ | $E_{1cm}^{1\%} = 1085$ |
| Inflexion towards 326 mμ | $E_{1cm}^{1\%} = 50$ |
| Inflexion towards 280 mμ | $E_{1cm}^{1\%} = 159$ |

As far as is known, this compound is not described in the literature.

EXAMPLE II

PREPARATION OF
5-methyl-10-(β-monomethylaminoethyl)-dibenzo (b,f) azepine . HCl

STEP A:
5-methyl-10-(β-N-ethoxycarbonyl-N-methylaminoethyl-dibenzo (b,f) azepine A solution of 6.5 gm of 5-methyl-10-(β-dimethylamino-ethyl)-dibenzo (b,f) azepine prepared as in Example I in 32.5 cc of benzene was added to a mixture of 32.5 cc of benzene and 6.5 cc of ethyl chloroformate and the mixture was refluxed for 5 hours. After cooling, ethyl acetate was added thereto and the reaction mixture was stirred with 1N hydrochloric acid. The organic phase was decanted off and was washed with water, dried over magnesium sulfate and distilled to dryness in vacuo to obtain 5 gm (64% yield) of 5-methyl-10-(β-N-methoxycarbonyl-N-methylaminoethyl)-dibenzo (b,f) azepine which was used as is for the next step.
I.R. SPECTRUM (chloroform)
Presence of carbonyl at 1687 cm$^{-1}$ As far as is known, this compound is not described in the literature.

STEP B:
5-methyl-10-(β-monomethylaminoethyl)-dibenzo (b,f) azepine . HCl 5 gm of 5-methyl-10-(β-N-ethoxycarbonyl-N-methylamino ethyl)dibenzo (b,f) azepine were added to a solution of 5 gm of potassium hydroxide in 50 cc of n-butanol and the mixture was stirred and heated at reflux for 20 hours. The n-butanol was distilled off under vacuum and the residue was taken up in water and extracted with ethylacetate. The organic phase was washed with water, dried over magnesium sulfate and distilled to dryness in vacuo. The residue was dissolved in 10 cc of ether and the solution was subjected to chromatography over magnesium silicate with elution with ether. The ether solution was distilled to dryness to obtain 3.5 gm of raw 5-methyl-10(β-monomethylaminoethyl)-dibenzo (b,f) azepine which were dissolved in 30 cc of ethyl acetate. A solution of anhydrous hydrochloric acid in ethyl acetate was added to the resulting solution and after icing for 30 minutes, the mixture was suction filtered. The precipitate was dried to obtain 3.5 gm of raw product which was purified by dissolution in refluxing benzene and concentration. After crystallization started, the mixture was vacuum filtered. The precipitate was washed with water and dried to obtain 2.65 gm of 5-methyl-10(β-monomethylaminoethyl)-dibenzo (b,f) azepine hydrochloride melting at 180°C.

The product occurred in the form of a yellow solid soluble in alcohols and methylene chloride, slightly soluble in benzene and ethylacetate and insoluble in ether and water.

Analysis: $C_{18}H_{21}N_2Cl$ ; molecular weight = 300.83
| | %C | %H | %N | %Cl |
|---|---|---|---|---|
| Calculated: | 71.87 | 7.04 | 9.31 | 11.79 |
| Found: | 72.1 | 6.7 | 9.2 | 11.8 |

As far as is known, this compound and its free base are not described in the literature.

EXAMPLE III

PREPARATION of
8-chloro-5-methyl-10-(β-dimethylaminoethyl)-dibenzo (b,f) azepine STEP A: 2-chloro-9-cyano-acridine A mixture of 1 gm of 2,9-dichloroacridine [obtained by the process of Bogucka, Roczniki, Chem. Vol. 40 (1966) p 677] 230 mg of sodium cyanide and 20 cc of methanol was heated for 4 hours at 140°C in a sealed tube and after cooling, the mixture was filtered. The precipitate was washed with acetone and dried. The product was purified by sublimation in vacuo at 0.1 mm Hg to obtain 530 mg of 2-chloro-9-cyano-acridine melting at 208°C.

The product occurred as a yellow solid soluble in chloroform, slightly soluble in alcohol and insoluble in water, ether and benzene.

Analysis: $C_{14}H_7N_2Cl$; molecular weight = 238.66
| | %C | %H | %N | %Cl |
|---|---|---|---|---|
| Calculated: | 70.47 | 2.95 | 11.74 | 14.86 |

| Found: | 71.2 | 3.3 | 11.5 | 14.6 |

IR SPECTRUM (chloroform)
Presence of conjugated CN at 2227 cm$^{-1}$, of aromatic, of C=C and conjugated -C=N

| UV SPECTRUM (chloroform) | |
|---|---|
| λ max. at 261–262 mµ | ε = 191,800 |
| λ max at 375 mµ | ε = 13,650 |
| λ max at 407 mµ | ε = 7,150 |

As far as is known, this compound is not described in the literature.

STEP B: 2-chloro-9-carboxy-acridine

A mixture of 19.8 gm of 2-chloro-9-cyano-acridine and 120 cc of 90% sulfuric acid was heated for 3 hours at 100°C and then cooled to 15°–20°C. A solution of 15 gm of sodium nitrite in 30 cc of water was added to the reaction mixture and the mixture was heated at 100°C for 2 hours. After cooling, the reaction mixture was added to a mixture of ice and water and then filtered. The precipitate was washed with water and extracted with a 10% aqueous sodium carbonate solution. The solution was made acidic by the addition of 6N hydrochloric acid, was filtered and the precipitate was washed with water and dried to obtain 10.6 gm of 2-chloro-9-carboxy-acridine melting at a temperature above 300°C. The product was used as such for the next step.

The product occurred in the form of a yellow solid soluble in dilute alkali solution and insoluble in water and the usual organic solvents.

As far as is known, this compound is not described in the literature.

STEP C: 2-chloro-9-methoxycarbonyl-acridine 4.9 gm of 2-chloro-9-carboxy-acridine were suspended in 5 cc of methylene chloride at room temperature and then 60 cc of a methylene chloride solution of diazomethane titrating 17.9 gm per liter was added thereto. The reaction mixture was then stirred for 90 minutes while bubbling nitrogen therethrough to eliminate excess diazomethane. The methylene chloride solution was washed with an aqueous solution of 10% sodium carbonate, then with water, dried over magnesium sulfate, treated with charcoal, filtered and then evaporated to dryness. The residue was recrystallized from boiling methanol to obtain 3.2 gm of 2-chloro-9-methoxycarbonyl-acridine melting at 130°C. The product occurred as a pale yellow solid soluble in chloroform, slightly soluble in ether and alcohol and insoluble in water.

| Analysis: C$_{15}$H$_{10}$ClNO$_2$; molecular weight = | | | |
|---|---|---|---|
| Calculated: %C 66.31 | %H 3.71 | %N 5.15 | %Cl 13.05 |
| Found: 66.4 | 3.7 | 5.4 | 13.2 |

IR SPECTRUM (chloroform)
Presence of ester at 1726 cm$^{-1}$, aromatic at 1626 cm$^{-1}$ and CN

| U.V. SPECTRUM | |
|---|---|
| λ max. at 256–257 mµ | ε = 157,000 |
| λ max. at 366 | ε = 10,840 |

As far as is known, this compound is not described in the literature.

STEP D: Methosulfate of 2-chloro-9-methoxycarbonyl-10-methyl-acridinium 5 gm of 2-chloro-9-methoxycarbonyl-acridine were dissolved in 25 cc of toluene and after 25 cc of methyl sulfate were added thereto, the reaction mixture was heated for 3 hours at 100°C. After cooling 50 cc of toluene were added and the mixture was filtered. The precipitate was washed with toluene and then ether and dried to obtain 5.4 gm of methosulfate of 2-chloro-9-methoxycarbonyl-10-methyl-acridinium which was used as is for the next step.

The compound occurred as a yellow solid melting at 248°C and was soluble in alcohol and chloroform, slightly soluble in ether and insoluble in water.

| Analysis: C$_{17}$H$_{16}$O$_6$NClS: molecular weight = 397.81 | | |
|---|---|---|
| Calculated: %Cl 8.91 | %S 8.05 | %N 3.51 |
| Found: 8.8 | 8.0 | 3.4 |

As far as is known, this compound is not described in the literature.

STEP E: 2-chloro-9-methoxycarbonyl-10-methyl-acridane 5.4 gm of the metho sulfate of 2-chloro-9-methoxycarbonyl-10-methyl-acridinium were suspended in 50 cc of methanol and 2.5 cc of water and after the addition of 5 gm of potassium borohydride, the temperature maintained at 35–40°C and the mixture was then stirred for 30 minutes at room temperature. The mixture was added to a mixture of ice and water and then filtered. The precipitate was washed with water and then iced methanol and dried to obtain 3.45 gm of 2-chloro-9-methoxycarbonyl-10-methyl-acridane melting at 166°C. The product occurred as a colorless solid soluble in alcohol and chloroform, slightly soluble in ether and insoluble in water. For analysis, the product was recrystallized from methyl ethylketone.

| Analysis: C$_{16}$H$_{14}$O$_2$NCl; molecular weight = 287.73 | |
|---|---|
| Calculated: %Cl 12.32 | %N 4.86 |
| Found: 12.5 | 4.6 |

IR SPECTRUM (CCl$_4$)
Presence of C=O at 1739 and 1734 cm$^{-1}$ and aromatic

| UV SPECTRUM (ethanol) | |
|---|---|
| λ max at 287 mµ | ε 16,900 |

As far as is known, this compound is not described in the literature.

STEP F:
2-chloro-9-methoxycarbonyl-9(β-dimethylaminoethyl)-10-methyl-acridane 3.9 gm of 2-chloro-9-methoxycarbonyl-10-methyl-acridane were dissolved in 10 cc of tetrahydrofuran and 5 cc of hexamethyl phosphortriamide and the solution was heated to 45°C and 3.4 gm of potassium tert.-butylate were added thereto. After stirring the mixture for 1 hour at 45°–47°C, 4.5 gm of β-dimethylaminoethyl chloride were added thereto and the mixture was stirred for 16 hours at 46°–48°C. After cooling the mixture, 150 cc of water were added and the mixture was extracted with ether. The organic phases were washed with an aqueous solution of sodium chloride, dried over magnesium sulfate, treated with charcoal, filtered and evaporated to dryness to obtain 4.2 gm of raw 2-chloro-9-methoxycarbonyl-9-(β-dimethylaminoethyl)-10-methyl-acridane.

4.2 gm of raw product were dissolved in 15 cc of methanol and after the addition of a solution of 1.24 gm of fumaric acid in 50 cc of methanol, the mixture was heated to reflux and the methanol distilled off was replaced with ethyl acetate. Ethyl acetate was evaporated off to the point of crystallization and the solution was iced for 1 hour and then filtered. The precipitate was washed with iced ethyl acetate and dried to obtain 4.1 gm of the fumarate of 2-chloro-9-methoxycarbonyl-9-(β-dimethylaminoethyl)-10-methyl-acridane. Concentration of the mother liquors gave a second crop of 0.2 gm of product. 4.3 gm of the said fumarate were suspended in 20 cc of water and the pH of the solution was adjusted to 8–9 by the addition of sodium hydroxide while stirring for 30 minutes. The solution was extracted with ether and the organic phase were washed with an aqueous solution of sodium chloride, dried over magnesium sulfate, filtered and evaporated to dryness to obtain 3.3 gm (67% yield) of 2-chloro-9-methoxycarbonyl-9-(β-dimethylaminoethyl)-10-methylacridane melting at 106°C. For analysis, the product was recrystallized from isopropyl ether.

The product was a colorless solid soluble in alcohol, ether and chloroform and insoluble in water.

Analysis: $C_{20}H_{23}N_2O_2Cl$; molecular weight = 358.85

| | %C | %H | %Cl | %N |
|---|---|---|---|---|
| Calculated | 66.95 | 6.45 | 9.88 | 7.81 |
| Found: | 67.0 | 6.3 | 9.8 | 7.9 |

IR SPECTRUM (CCl₄)
presence of ester, aromatic ring and

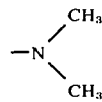

As far as is known, this compound is not described in the literature.

STEP G:
2-chloro-9-hydroxymethyl-9-(β-dimethylaminoethyl) 10-methyl acridane 14 cc of tetrahydrofuran were cooled to 0°C and 0.9 gm of lithium aluminum hydride and then a solution of 1.4 gm of 2-chloro-9-methoxycarbonyl-9-(β-dimethylaminoethyl)-10-methyl-acridane in 14 cc of tetrahydrofuran were added thereto while maintaining the temperature below +10°C. The reaction mixture was then heated at reflux for 2½ hours and cooled to 0°, +5°C and 10 cc of tetrahydrofuran containing 20% water and then 50 cc of water were added thereto. The reaction mixture was extracted with methylene chloride and filtered. The organic phases were washed with an aqueous solution of sodium chloride, dried over magnesium sulfate and evaporated to dryness to obtain 1.15 gm of 2-chloro-9-hydroxymethyl-9-(β-dimethylaminoethyl)-10-methyl-acridane which was used as is for the next step.

For analysis, the product was recrystallized from 20 volumes of isopropyl ether. The compound occurred in the form of a colorless solid soluble in ether, alcohol and chloroform and insoluble in water. It had a melting point of about 100°C.

Analysis: $C_{19}H_{23}N_2OCl$; molecular weight = 330.84

| | %C | %H | %N | %Cl |
|---|---|---|---|---|
| Calculated: | 68.98 | 7.00 | 8.46 | 10.72 |
| Found: | 69.3 | 7.4 | 7.6 | 9.8 |

IR SPECTRUM
Presence of OH, aromatic ring and (b,f)

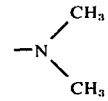

As far as is known, this compound is not described in the literature.

STEP H:
8-chloro-5-methyl-10-(β-dimethylaminoethyl)dibenzo (b,f) azepine

A mixture of 5 gm of 2-chloro-9-hydroxymethyl-9-(β-dimethylaminoethyl)-10-methyl-acridane, 150 cc of xylene and 25 gm of phosphoric acid anhydride was refluxed for 3 hours under a nitrogen atmosphere and after cooling, the reaction mixture was poured into a water-ice mixture. The mixture was made alkaline by the addition of 35 cc sodium hydroxide solution and was extracted with ethyl acetate. The organic phase was washed with an aqueous sodium chloride solution, dried over magnesium sulfate, treated with charcoal, filtered and evaporated to dryness to obtain 3.9 gm of raw 8-chloro-5-methyl-10-(β-dimethylaminoethyl)-dibenzo (b,f) azepine. The 3.9 gm of raw product were dissolved in 15 cc of methanol and a solution of 1.2 gm of fumaric acid in 45 cc of methanol was added thereto. The methanol was distilled off and replaced with ethyl acetate and the mixture was then refrigerated for 48 hours for crystallization and filtered. The precipitate was washed with ethyl acetate and dried to obtain 2.8 gm, the fumarate of 8-chloro-5-methyl-10-(β-dimethylaminoethyl)-dibenzo (b,f) azepine melting at 150°C, then 164°C. Cooling of the mother liquors gave a second crop of 0.25 g of product.

The 3.05 gm of fumarate product were dissolved in 20 cc of water which was made alkaline with sodium hydroxide solution. After extraction with ether, the organic phases were washed with an aqueous solution of sodium chloride, dried over magnesium sulfate and evaporated to dryness. The residue was recrystallized from hot pentane to obtain 1.72 gm of 8-chloro-5- methyl-10-(β-dimethylaminoethyl)-dibenzo(b,f)azepine melting at 82°C. The solid yellow product was soluble in alcohol, ether and chloroform and insoluble in water.

Analysis: $C_{19}H_{21}N_2Cl$; molecular weight = 312.83
Calculated: %C 72.95  %H 6.76  %N 8.95  %Cl 11.34
Found:      73.2       6.9       8.8      11.3

IR Spectrum (CCl₄):
Presence of C = C at 1627 cm$^{-1}$ and aromatic ring at 1593 and 1573 cm$^{-1}$ UV Spectrum (ethanol)
λ max. at 217 mμ    ε = 28,200
λ max. at 257 mμ    ε = 32,790

As far as is known, this compound is not described in the literature.

EXAMPLE IV

PREPARATION OF 2-chloro-5-methyl-10-(β-dimethylaminoethyl)-dibenzo (b,f)azepine The mother liquors of crystallization of the fumarate of Step H of Example III were dried and made alkaline by addition of sodium hydroxide solution. The mixture was then extracted twice with ether and the combined separated ether phase was washed with salt water and dried over magnesium sulfate and concentrated. 1.7 gm of a raw product distinct from the compound of Example III by thin-layer chromatography was collected. By chromatography over silica gel and elution with a mixture of triethylamine-chloroform-cyclohexane, there was separated again 0.4 gm of the compound of Example III melting at 79°C and then 0.5 gm of a new compound which was a position isomer of the compound of Example III, namely 2-chloro-5-methyl-10-(β-dimethylaminoethyl)-dibenzo (b,f) azepine having the following physical constants:

U.V. Spectrum (ethanol)
λ max. at 217 mμ    ε = 26,500
λ max. at 257 mμ    ε = 34,000

Inflexion towards 285 mμ
λ max at 337 mμ
RMN Spectrum
Modifications in the ethylenic and aromatic proton regions relative to the compound of Example III.

Analysis: $C_{19}H_{21}N_2Cl$, molecular weight = 312.83
Calculated:    %Cl 11.34    %N 8.95
Found:         10.7         8.6

As far as is known, this compound is not described in the literature.

EXAMPLE V

PREPARATION OF 7-chloro-5-methyl-10-(β-dimethylaminoethyl-dibenzo (b,f) azepine STEP A: 3-chloro-9-methoxycarbonyl-acridine 5.7 gm of 3-chloro-9-carboxy-acridine [obtained by the process of Craig et al, J. Org. Chem. Soc., Vol. 26 (1961) p. 135] were suspended in 50 cc of methylene chloride which was refrigerated and to which 200 cc of a solution of diazomethane in methylene chloride was added. After stirring for 15 minutes at 0°C, the mixture was filtered and distilled to dryness under vacuum. The residue was dissolved in 200 cc of refluxing methanol and the solution was filtered, concentrated to about 50 cc, iced for 1 hour and filtered. The precipitate was washed with water and dried to obtain 4.75 gm of 3-chloro-9-methoxycarbonyl-acridine melting at 148°C. The product was a yellow solid slightly soluble in methanol and insoluble in water. For analysis, the product was recrystallized from hot and cold methanol without any change in its melting point.

Analysis: $C_{15}H_{10}O_2NCl$; molecular weight = 271.71
Calculated: %C 66.31  %H 3.71  %Cl 13.05  %N 5.15
Found:      66.0       3.9       13.1       5.0

IR SPECTRUM (CCl₄)
Presence of C = 0 at 1732 cm$^{-1}$ and aromatic ring.
As far as it is known, this compound is not described in the literature.

STEP B: Methosulfate of 3-chloro-9-methoxycarbonyl-10-methyl-acridinium

A mixture of 21 gm of 3-chloro-9-methoxycarbonyl-acridine and 100 cc of methyl sulfate was heated for 3 hours at 100°C with stirring and after refrigeration, 20 cc of toluene and then 400 cc of ether were added thereto. The mixture was filtered and the precipitate was washed with ether and dried in vacuo to obtain 28.1 gm of the methosulfate of 3-chloro-9-methoxycarbonyl-10-methyl-acridinium which was used as is for the next step.

The product was a yellow solid melting at about 250°C and was soluble in methanol, slightly soluble in toluene and insoluble in ether and water.

Analysis: $C_{17}H_{16}O_6NClS$, molecular weight = 393.87
Calculated:  %N 3.56    %Cl 9.00    %S 7.13
Found:       3.5         8.8         8.0

As far as is known, this compound is not described in the literature.

STEP C: 3-chloro-9-methoxy-carbonyl-10-methyl-acridane 5.3 gm of the methosulfate of 3-chloro-9-methoxycarbonyl-10-methyl-acridinium were added to a mixture of 50 cc of ethanol and 2.5 cc of water and after the addition of 5.3 gm potassium borohydride while maintaining a 25°C temperature, the mixture was stirred for 30 minutes and poured into water. After stirring for 30 minutes, the mixture was extracted with ether and the ether phase was washed with water, dried over magnesium sulfate and distilled to dryness in vacuo. The residue was dissolved in 30 cc of refluxing isopropyl ether, filtered and concentrated to 20 cc. The mixture was iced for 30 minutes and filtered. The precipitate was washed with iced isopropyl ether and dried in vacuo to obtain 3.18 gm of 3-chloro-9-methoxycarbonyl-10-methyl-acridane which was used as is for the next step.

The compound was a colorless solid melting at 118°C and was soluble in chlorinated solvents, alcohols and ethyl acetate and insoluble in water. For analysis, the product was recrystallized from hot and cold isopropyl ether without any change in melting point.

Analysis: $C_{16}H_{14}O_2NCl$; molecular weight = 287.76
Calculated: %C 66.79 %H 4.90 %N 4.87 %Cl 12.32
Found: 66.8 5.1 4.8 12.3

IR Spectrum (CCl$_4$)
Presence of ester carbonyl at 1739 and 1732 cm$^{-1}$ and aromatic ring.

UV Spectrum (ethanol)
λ max at 214 mμ    $E_{1cm}^{1\%} = 1155$
inflexion towards 311 mμ    $E_{1cm}^{1\%} = 234$
λ max at 286 mμ    $E_{1cm}^{1\%} = 519$ or $\epsilon = 14,950$ As far as is known, this compound is not described in the literature.

STEP D: Fumarate of 3-chloro-9-methoxycarbonyl-9-(β-dimethylaminoethyl)-10-methyl-acridane 10 gm of 3-chloro-9-methoxycarbonyl-10-methyl-acridane were added to a mixture of 75 cc of tetrahydrofuran and 25 cc of hexamethyl phosphortriamide and 4.6 gm of potassium tertbutylate were added thereto at room temperature and the mixture was stirred for 30 minutes. After refrigeration, 15 cc of β-dimethylaminoethyl chloride were added at a temperature less than 10°C and temperature of the reaction mixture was allowed to rise to room temperature. The reaction mixture was allowed to stand for 16 hours and then was added to water and extracted with ethyl acetate. The organic phase was washed with water, dried over magnesium sulfate and distilled to dryness in vacuo.

The residue was dissolved in 25 cc of methanol and after the addition of a solution of 4 gm of fumaric acid in 150 cc of methanol, the mixture was distilled and the methanol taken off was replaced with ethylacetate. The ethylacetate mixture was concentrated to 25 cc and crystallization began. After icing for 30 minutes, the mixture was filtered and the precipitate was washed with water and dried in vacuo to obtain 10.1 gm of the fumarate of 3-chloro-9-methoxycarbonyl-9-(β-dimethylaminoethyl)-10-methyl-acridane which was utilized as is for the next step.

For analysis, 500 mg of the fumarate were dissolved in 5 cc of refluxing methanol and after the addition of 25 cc of ethyl acetate, the mixture filtered. The methanol was distilled off and the ethyl acetate was concentrated to a small volume and iced for 30 minutes. After filtering, the precipitate was washed with water and dried in vacuo to obtain 420 mg of the fumarate of 3-chloro-9-methoxycarbonyl-9-(β-dimethylaminoethyl)-10-methyl-acridane melting at 192°C. The colorless solid was soluble in methanol, slightly soluble in chlorinated solvents and insoluble in water.

Analysis: $C_{24}H_{27}O_6N_2Cl$; molecular weight = 474.95
Calculated: %C 60.69 %H 5.73 %N 5.90 %Cl 7.46
Found: 60.8 5.9 5.6 7.5

IR SPECTRUM (Nujol)
Presence of ester carbonyl at 1727 cm$^{-1}$, acid carbonyl at 1711 cm$^{-1}$, COO— at 1588 cm$^{-1}$ and aromatic ring.

U.V. SPECTRUM (ethanol)
λ max. at 211 mμ    $E_{1cm}^{1\%} = 1,020$ $\epsilon = 48,450$
λ max at 290 mμ    $E_{1cm}^{1\%} = 330$ $\epsilon = 15,650$
Inflexion towards 312 mμ    $E_{1cm}^{1\%} = 16$ As far as is known, this compound is not described in the literature.

STEP E: 3-chloro-9-hydroxymethyl-9-(β-dimethylaminoethyl)-10-methyl-acridane 25.7 gm of the fumarate of 3-chloro-9-methoxy-carbonyl-9-(β-dimethylaminoethyl)-10-methyl-acridane were suspended in 250 cc of water and after refrigeration, 25 cc of sodium hydroxide solution were added. The mixture was extracted with methylene chloride and the organic phase was washed with water, dried over magnesium sulfate and distilled to dryness in vacuo to obtain 20 gm of 3-chloro-9-methoxycarbonyl-9-(β-dimethylaminoethyl)-10-methylacridane. First 10 gm of lithium aluminum hydride and then 20 gm of 3-chloro-9-methoxycarbonyl-9-(β-dimethylaminoethyl)-10-methylacridane in solution in 200 cc of tetrahydrofuran were added to 200 cc of cold tetrahydrofuran at a temperature below 10°C and after stirring for 10 minutes at 0°C, it was refluxed for 15 minutes. After cooling the reaction mixture, excess reactants were decomposed by 200 cc of tetrahydrofuran containing 20% of water at a temperature below 10°C. After filtering and distilling the mixture to dryness in vacuo, the residue was dissolved in methylene chloride and the solution was washed with water, dried over magnesium sulfate and distilled to dryness in vacuo. The residue was dissolved in 80 cc of ethyl acetate and the resulting solution was filtered and concentrated to 50 cc after which crystallization began. After being iced for 30 minutes, the mixture was filtered and the precipitate was washed with ethyl acetate and then ether and dried to obtain 14.35 gm of 3-chloro-9-hydroxymethyl-9-(β-dimethylaminoethyl)-10-methyl-acridane melting at 120°C.

For analysis, the product was recrystallized from hot and cold ethyl acetate. The compound was a colorless solid soluble in methanol, slightly soluble in ether and insoluble in water.

Analysis: $C_{19}H_{23}ON_2Cl$; molecular weight = 330.87
Calculated %C 68.97 %H 7.01 %N 8.47 %Cl 10.72
Found: 68.7 7.3 8.3 10.9

IR SPECTRUM (CCl$_4$)
Presence of OH and aromatic ring

| UV SPECTRUM | |
|---|---|
| λ max at 215 mμ | $E_{1cm}^{1\%} = 944$ |
| inflexion towards 237 mμ | $E_{1cm}^{1\%} = 260$ |
| λ max at 291 mμ | $E_{1cm}^{1\%} = 471$  $\epsilon = 15,550$ |
| Inflexion towards 311 mμ | $E_{1cm}^{1\%} = 249$ |

As far as is known, this compound is not described in the literature.

STEP F:
7-chloro-5-methyl-10(β-dimethylaminoethyl)-dibenzo (b,f) azepine

A mixture of 5 gm of 3-chloro-9-hydroxymethyl-9(β-dimethylaminoethyl)-10-methyl-acridane, 200 cc of xylene and 25 gm of phosphoric acid anhydride was refluxed for 3 hours with stirring and after cooling, the reaction mixture was poured over ice. The resulting mixture was made alkaline by the addition of 50 cc of sodium hydroxide solution and was extracted with ethyl acetate. The organic phase was washed with water, dried over magnesium sulfate and distilled to dryness in vacuo. The residue was subjected to chromatography over silica gel with elution with a 6-3-1 mixture of cyclohexane-chloroform-triethylamine. Evaporation of the solvent gave 4.15 gm of 7-chloro-5-methyl-10-(β-dimethylaminoethyl)-dibenzo (b,f) azepine. The product was amorphous and was soluble in alcohols, chlorinated solvents, ether and benzene and insoluble in water.

Analysis: $C_{19}H_{21}N_2Cl$; molecular weight = 312.85
| | | |
|---|---|---|
| Calculated: | %N 8.95 | %Cl 11.33 |
| Found: | 9.0 | 11.6 |

IR Spectrum (CCl₄)
Presence of aromatic substituted with a heteroatom and of

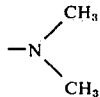

RMN spectrum favored the desired structure but did not completely exclude possibility of presence of isomeric compound.

As far as is known, this compound is not described in the literature.

EXAMPLE VI

PREPARATION OF FUMARATE OF
7-chloro-5-methyl-10-(β-monomethylaminoethyl)-dibenzo (b,f) azepine STEP A: 7-chloro 5-methyl 10-(β-N-ethoxycarbonyl N-methylaminoethyl) dibenzo (b,f)azepine A solution of 8 gm of 7-chloro-5-methyl-10-(β-dimethylaminoethyl)-dibenzo (b,f) azepine in 40 cc of benzene was added to a mixture of 40 cc of benzene and 8 cc of ethyl chloroformate and the mixture was heated at reflux for 5 hours. After refrigeration, the benzene solution was washed with 2N hydrochloric acid and then water, dried over magnesium sulfate and distilled to dryness in vacuo to obtain 9 gm of 7-chloro-5-methyl-10-(β-N-ethoxycarbonyl-N-methylaminoethyl)-dibenzo (b,f) azepine which was used as is for the next step.

As far as is known, this compound is not described in the literature.

STEP B: Fumarate of
7-chloro-5-methyl-10-(β-monomethylaminoethyl)-dibenzo (b,f) azepine 10 gm of 7-chloro-5-methyl-10-(β-N-ethoxycarbonyl-N-methylamino ethyl) dibenzo (b,f) azepine in solution in 10 gm of potassium carbonate pellets and 100 cc of butanol was refluxed for 20 hours and the butanol was distilled off in vacuo. The residue was taken up in ether and the ether phase was washed with water and extracted with 2N hydrochloric acid. The acid solution was washed with ether and made alkaline by addition of sodium hydroxide solution while stirring and was then extracted with ether. The ether extracts were washed with water, dried over magnesium sulfate and distilled to dryness in vacuo to obtain 6.8 gm of 7-chloro-5-methyl-10-(β-monomethylaminoethyl)-dibenzo (b,f) azepine which was purified by chromatography over silica gel with elution with a mixture of chloroform-acetone-triethylamine (6-3-1).

IR SPECTRUM
Presence of —NH at 3303 cm⁻¹, aromatic ring at 1588 cm⁻¹ and C = C at 1563 and 1630 cm$^{116}$ ¹.

As far as is known, this compound is not described in the literature.

4 gm of 7-chloro-5-methyl-10-(β-monomethylaminoethyl)-dibenzo (b,f) azepine were dissolved in 10 cc of methanol and then a solution of 1.55 gm of fumaric acid in 40 cc of methanol was added thereto. After filtration, the methanol was distilled off and replaced with ethyl acetate until the start of a slight turbidity. Crystallization was induced by scratching and the mixture was iced for 30 minutes and filtered. The precipitate was washed with ethyl acetate containing 20% of methanol and dried under vacuum to obtain 4 gm of the fumarate of 7-chloro-5-methyl-10-(β-monomethylaminoethyl)-dibenzo (b,f) azepine melting at 180°C.

The product occurred in the form of yellow crystals soluble in methanol and ethanol, and slightly soluble in water and chlorinated solvents. For analysis, the product was recrystallized from methanol with no melting point change.

Analysis: $C_{22}H_{23}O_4N_2Cl$: molecular weight = 414.89
| | | | | |
|---|---|---|---|---|
| Calculated: | %C 63.69 | %H 5.59 | %N 6.75 | %Cl 8.54 |
| Found: | 63.7 | 5.6 | 6.4 | 8.5 |

IR SPECTRUM (Nujol)
Presence of carbonyl at 1705 cm⁻¹, C = C at 1634 cm⁻¹, of COO θ, aromatic ring, NH₂ and acid hydroxyl.

| U.V. SPECTRUM (ethanol): | |
|---|---|
| λ max. at 214 mμ | $\epsilon = 37,000$ |
| λ max. at 255–256 mμ | $\epsilon = 32,600$ |
| inflexion towards 326 mμ | $E_{1cm}^{1\%} = 39$ |

As far as is known, this compound is not described in the literature.

PHARMACOLOGICAL STUDY A. Anti-depressant Activity

The anti-depressant activity was determined by the eyelid ptosis test codified by Rubin, J. Pharm. Exp. Ther. Vol. 120 (1957), p. 125. Because of the antagonistic activity of anti-depressants towards reserpine, the degree of ptosis drops as the administered dose is increased and has a zero value if ptosis does not appear after the standard dose of reserpine. The eyelid ptosis test is used as a quantitative evaluation of the animal's condition but the antagonism is equally exerted on all the neuro-depressive symptoms of reserpine: immobility, adynamia, hypothermia, myosis, etc. The readings were effected 4 hours after the intraperitoneal injection of 1 mg/kg of reserpine to groups of rats which had received an intraperitoneal injection of the test compound 1 hour earlier. The results of Table I are expressed as percent of ptosis compared to the controls receiving reserpine only.

TABLE I

| Test Compound | Dose in mg/kg | % of ptosis |
|---|---|---|
| 5-methyl-10-($\beta$-di-methylamino ethyl)-dibenzo (b,f) azepine | 2 | 100 |
| | 5 | 59 |
| | 10 | 37 |
| | 20 | 30 |
| 5-methyl-10-($\beta$-monomethylaminoethyl)-dibenzo (b,f) azepine hydrochloride | 1 | 100 |
| | 2 | 72 |
| | 5 | 50 |
| | 10 | 33 |
| | 20 | 11 |

Table I shows that the dose that reduces eyelid ptosis caused by reserpine by 50% is about 5 mg/kg for both products.

B. ACUTE TOXICITY DETERMINATION

The two products were administered intraperitoneally to groups of Rockland mice weighing between 18–22 g and the animals were observed for 7 days. The LD$_{50}$ (50% of animals died) was about 50 mg/kg for 5-methyl-10-($\beta$-dimethylaminoethyl)-dibenzo (b,f) azepine and about 75 mg/kg for 5-methyl-10($\beta$-monomethylaminoethyl)-dibenzo (b,f) azepine hydrochloride.

Various modifications of the products and compositions of the invention may be made without departing from the spirit or scope thereof and it is to be understood that the invention is to be limited only as defined in the appended claims.

We claim:

1. A thymoanaleptic composition comprising 25 to 100 mg of a compound selected from the group consisting of 5-methyl-10-($\beta$-alkylaminoethyl) dibenzo (b,f) azepine of the formula

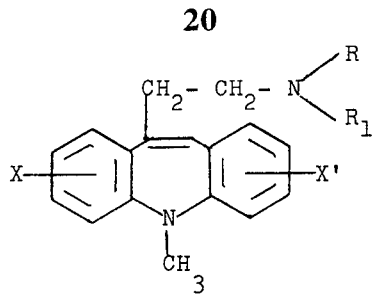

wherein R is lower alkyl, R$_1$ is selected from the group consisting of hydrogen and lower alkyl and X and X' are selected from the group consisting of hydrogen and halogen and its non-toxic, pharmaceutically acceptable acid addition salt and a pharmaceutical carrier.

2. A method of inducing thymoanaleptic activity in warm-blooded animals which comprises administering to warm-blooded animals an amount effective to induce thymoanaleptic activity of a compound selected from the group consisting of 5-methyl-10-($\beta$-alkylaminoethyl) dibenzo (b,f) azepine of the formula

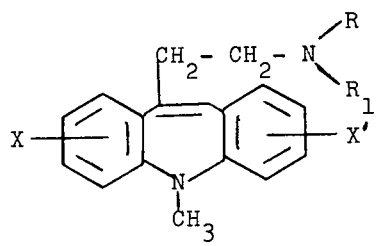

wherein R is lower alkyl, R$_1$ is selected from the group consisting of hydrogen and lower alkyl and X and X' are selected from the group consisting of hydrogen and halogen and its non-toxic, pharmaceutically acceptable acid addition salt.

3. The method of claim 2 wherein X and X' are selected from the group consisting of hydrogen, chlorine, bromine and iodine.

4. The method of claim 2 wherein R is alkyl of 1 to 4 carbon atoms and R$_1$ is selected from the group consisting of hydrogen and alkyl of 1 to 4 carbon atoms.

5. The method of claim 2 selected from the group consisting of 5-methyl-10-($\beta$-dimethylaminethyl)-dibenzo (b,f) azepine and the hydrochloride salt.

6. The method of claim 2 selected from the group consisting of 5-methyl-10-($\beta$-monomethylaminoethyl)-dibenzo (b,f) azepine and the hydrochloride salt.

7. The method of claim 2 selected from the group consisting of 2-chloro-5-methyl-10-($\beta$-dimethylaminoethyl)-dibenzo (b,f) azepine and the fumarate salt.

8. The method of claim 2 selected from the group consisting of 7-chloro-5-methyl-10-($\beta$-dimethylaminoethyl)-dibenzo (b,f,) azepine and the fumarate salt.

9. The method of claim 2 selected from the group consisting of 7-chloro-5-methyl-10-($\beta$-monomethylaminoethyl)-dibenzo (b,f) azepine and the fumarate salt.

10. The method of claim 2 selected from the group consisting of 8-chloro-5-methyl-10-($\beta$-dimethylaminoethyl)-dibenzo (b,f) azepine and the furamate salt.

* * * * *